United States Patent
Vial et al.

(10) Patent No.: US 11,352,314 B2
(45) Date of Patent: **\*Jun. 7, 2022**

(54) FRUITY ODORANT

(71) Applicant: FIRMENICH SA, Satigny (CH)

(72) Inventors: Christian Vial, Satigny (CH); Roger Leslie Snowden, Satigny (CH)

(73) Assignee: FIRMENICH SA, Satigny (CH)

( \* ) Notice: Subject to any disclaimer, the term of this patent is extended or adjusted under 35 U.S.C. 154(b) by 22 days.

This patent is subject to a terminal disclaimer.

(21) Appl. No.: 16/922,799

(22) Filed: Jul. 7, 2020

(65) Prior Publication Data

US 2020/0339500 A1     Oct. 29, 2020

Related U.S. Application Data

(60) Division of application No. 16/184,532, filed on Nov. 8, 2018, now Pat. No. 10,766,850, which is a continuation of application No. 15/927,287, filed on Mar. 21, 2018, now Pat. No. 10,246,402, which is a continuation of application No. 12/991,506, filed as application No. PCT/IB2009/052171 on May 25, 2009, now Pat. No. 9,957,221.

(30) Foreign Application Priority Data

Jun. 4, 2008    (WO) ................. PCT/IB2008/052179

(51) Int. Cl.
*C07C 69/67*     (2006.01)
*C11B 9/00*      (2006.01)

(52) U.S. Cl.
CPC .......... *C07C 69/67* (2013.01); *C11B 9/0019* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 6,509,312 B1 | 1/2003 | Giersch | |
| 9,957,221 B2 * | 5/2018 | Vial | .................... C11B 9/0019 |
| 10,047,319 B2 * | 8/2018 | Vial | .................... C11B 9/0019 |
| 10,246,402 B2 * | 4/2019 | Vial | .................... C11B 9/0019 |
| 10,766,850 B2 * | 9/2020 | Vial | .................... C11B 9/0019 |

FOREIGN PATENT DOCUMENTS

| | | |
|---|---|---|
| JP | H38113795 A | 5/1996 |
| JP | 2005143465 A | 6/2005 |
| JP | 2006020526 A | 1/2006 |
| JP | 2006124490 A | 5/2006 |
| WO | 2008006058 A2 | 1/2008 |

OTHER PUBLICATIONS

International Search Report and Written Opinion of corresponding PCT/IB2009/052171, dated Aug. 13, 2009.
Rowe, "Aroma Chemicals I: C, H, Compounds," Chemistry and Technology of Flavours and Fragrances, Blackwell publishing, p. 63, 1st paragraph (2005).
Schreier, "Wine Aroma composition: Identification of additional volatile constituents of red wine," J. Agric. Food Chem., 28:926-928 (1980).
Teai et al., Volatile Compounds in Fresh Pulp of Pineapple (*Ananas comosus* [L.] Merr.) from French Polynesia, J. Essent. Oil. Res., 13:314-318 (2001).
Wagner et al., "N-Acylpyridinium Trifluoromethanesulfonates and Tetrafluoroborates: Shuttle Reagents for the Acylation of Enantiopure Secondary Alcohol," Synthesis, 1998(6):883-888 (1998).

\* cited by examiner

*Primary Examiner* — Erin E Hirt
(74) *Attorney, Agent, or Firm* — Armstrong Teasdale LLP

(57) ABSTRACT

The present invention relates to compounds of formula (I) that are useful as perfuming ingredients of the fruity type. Formula (I) is

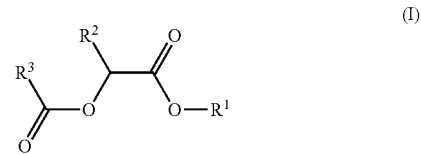

in the form of any one of its stereoisomers or of a mixture thereof, wherein $R^1$ represents a $C_{1-3}$ alkyl or alkenyl group, $R^2$ represents a methyl or ethyl group, $R^3$ represents a $C_{1-4}$ alkyl or alkenyl group, and the compound (I) has from 8 to 12 carbon atoms.

11 Claims, No Drawings

FRUITY ODORANT

CROSS-REFERENCE TO RELATED APPLICATIONS

This application is a divisional of U.S. application Ser. No. 16/184,532, filed Nov. 8, 2018, which is a continuation of U.S. application Ser. No. 15/927,287 filed Mar. 21, 2018, now U.S. Pat. No. 10,246,402, which is a continuation of U.S. application Ser. No. 12/991,506, filed Nov. 8, 2010, now U.S. Pat. No. 9,957,221, which is a 371 filing of International Application No. PCT/IB2009/052171, filed May 25, 2009, which claims the benefit of International Application No. PCT/IB2008/052179, filed Jun. 4, 2008, the disclosures of which are hereby incorporated by reference as if written herein in their entirety.

TECHNICAL FIELD

The present invention relates to the field of perfumery. More particularly, it concerns some di-ester compounds which possess a fruity odor.

The present invention concerns the use of said compounds in the perfumery industry as well as the compositions or articles containing said compounds.

PRIOR ART

To the best of our knowledge, none of the invention's compounds have been reported or suggested as perfuming ingredient. In some instance, some invention's compounds have been reported in the context of synthesis.

Some analogues are reported in the literature as flavoring ingredients. In particular, one may cite ethyl acetyl lactate (reported in http://www.thegoodscentscompany.com/data/rw1582561.html) and is described only for flavoring uses. This compound is reported also as one of the many constituents of pineapple (see Journal of Essential Oil Research, 2001, 13, 314).

However, these prior art documents do not report or suggest any organoleptic properties of the compounds of formula (I), or any use of said compounds in the field of perfumery.

DESCRIPTION OF THE INVENTION

We have now surprisingly discovered that a compound of formula

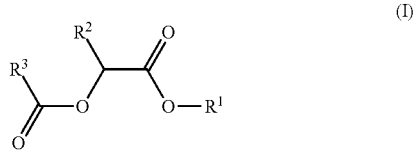

(I)

in the form of any one of its stereoisomers or of a mixture thereof, and wherein $R^1$ represents a $C_{1-3}$ alkyl or alkenyl group, $R^2$ represents a methyl or ethyl group, $R^3$ represents a $C_{1-4}$ alkyl or alkenyl group, and said compound (I) has from 8 to 12 carbon atoms; can be used as perfuming ingredient, for instance to impart odor notes of the fruity type.

According to a particular embodiment of the invention, said compound (I) is a $C_8$ or $C_{10}$ compound.

According to a particular embodiment of the invention, said $R^1$ group may represent a $C_2$ or $C_3$ alkyl group, e.g. ethyl or n-propyl or iso-propyl.

According to a particular embodiment of the invention, said $R^2$ group may represent a methyl group.

According to a particular embodiment of the invention, said $R^3$ group may represent a $C_{2-4}$ alkyl group, e.g. ethyl or n-propyl, iso-propyl or ter-butyl.

According to a particular embodiment of the invention, said $R^1$ group represents a $C_2$ or $C_3$ alkyl group, $R^2$ represents a methyl group, $R^3$ represents a $C_{1-4}$ alkyl group, and one of said $R^1$ or $R^3$ represents a branched alkyl group and the other a linear alkyl group.

A compound of formula (I), having 10 carbon atoms and wherein all $R^1$, $R^2$ and $R^3$ are alkyl groups, is also a novel compound, provided that (1S)-2-ethoxy-l-methyl-2-oxo-ethyl pyruvate is excluded, and is therefore another aspect of the present invention.

As non-limiting example of invention's compounds one may cite (−)-propyl (2S)-2-(isobutyryloxy)propanoate, which represents a preferred embodiment of the invention, and possesses a velvety fruity-apricot/mirabelle type note.

In fact, it has been found that this compound can be used also to impart fruity-apricot odor as top-note, said top note being fresh, ethery reminding of the apricot peel rather than an alimentary note. This top note is quite surprising, indeed, other known apricot type compounds, such as the lactones (e.g. undecalactone gamma) or Veloutone (2,2,5-trimethyl-5-pentyl-1-cyclopentanone; origin: Firmenich SA), are known to impart only bottom-notes of the apricot type with a strong alimentary aspect.

Furthermore, one may also mention (−)—(S)-1-(ethoxycarbonyl)ethyl pivalate, which possesses a fruity-aromatic odor, close to the one of isopentyrate (1,3-dimethyl-3-butenyl isobutyrate; origin: Firmenich SA), a known perfuming ingredient.

Another example of invention's compounds is represented by (−)-ethyl (S)-2-(propanoyloxy)propanoate, which possesses a fruity-vinous note with a floral aspect.

When the odor of these invention's compounds is compared with that of the prior art (i.e., ethyl 2-acetoxyopropanoate), then the invention's compounds distinguish themselves by clearly lacking the herbaceous note which is characteristic of the prior art compound. This is also the case of all the invention's compounds.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said composition, which in fact can be advantageously employed as perfuming ingredient, is also an object of the present invention.

Therefore, another object of the present invention is a perfuming composition comprising:

i) as perfuming ingredient, at least one invention's compound as defined above;

ii) at least one ingredient selected from the group consisting of a perfumery carrier and a perfumery base; and iii) optionally at least one perfumery adjuvant.

By "perfumery carrier" we mean here a material which is practically neutral from a perfumery point of view, i.e., that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words, such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:

i) as perfuming ingredient, at least one compound of formula (I), as defined above, or an invention's perfuming composition; and ii) a consumer product base; is also a feature of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.1% to 20% by weight, or even more, of the compounds of the invention based on the weight of the composition into which they are incorporated. Concentrations lower than these, such as in the order of 0.001% to 1% by weight, can be used when these compounds are incorporated into perfumed articles, percentage being relative to the weight of the article.

The invention's compounds can be prepared according to a method as described herein below in the Examples.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts δ are indicated in ppm with respect to TMS as standard, the coupling constants J are expressed in Hz.

Example 1

Synthesis of compounds of formula (I)

Preparation of (−)-propyl (2S)-2-(isobutyryloxy)propanoate

To a solution of (−)-propyl lactate (26.44 g, 0.2 mole, $[\alpha]^{20}_D$=−6° (1.6%, CHCl$_3$), triethylamine (30.36 g, 0.3 mole) in dichloromethane (300 ml) at 0° was slowly added isobutyryl chloride (32.44 g, 0.3 mole). After 30 minutes at 0° and 2.5 hours at room temperature, the mixture was quenched with 250 ml of iced 7% aqueous HCl and then the organic phase was washed with aqueous bicarbonate, water and dried over sodium sulphate. Evaporation of the dichloromethane provided a residue which was fractionated using a Fischer column to give 31.26 g (B.p.$_{10mbars}$=93-94°, yield=77.3%) of >99% pure (−)-propyl-(2S)-2-(isobutyryloxy)-propanoate.

$[\alpha]^{20}_D$=−38° (2.5%, CHCl$_3$).

$^1$H-NMR (400 MHz, CDCl$_3$): 0.94 (t: J=7, 3H); 1.19 (d: J=7, 3H); 1.22 (d: J=7, 3H); 1.49 (d: J=7, 3H); 1.67 (m, 2H), 2.63 (m, 1H), 4.10 (m, 2H), 5.07 (q: J=7, 1H). $^{13}$C-NMR (100 MHz, CDCl$_3$): 10.3 (q), 17.0 (q), 18.7 (q), 18.9 (q), 21.9 (t), 33.7 (d), 66.8 (t), 68.4 (d), 171.0 (s), 176.5 (s).

Preparation of (−)-ethyl (S)-2-(propanoyloxy)propanoate
(−)-Ethyl lactate (20.0 g, 0.17mole, $[\alpha]^{20}_D$=−10.5° (neat)) was esterified with propionyl chloride as described before. (B.p.$_{1mbar}$=31°, yield=83%)
$[\alpha]^{20}_D$=−47.5° (2.0%, CHCl$_3$).
$^1$H-NMR: 1.17 (t, J=7, 3H); 1.28 (t, J=7, 3H); 1.48 (d, J=7, 3H); 2.41 (m, 2H); 4.20 (q, J=7, 2H); 5.07 (q, J=7, 1H).
$^{13}$C-NMR: 9.0 (q), 14.1 (q), 16.9 (q), 27.3 (t), 61.3 (t), 68.5 (d), 171.0 (s), 173.8 (s).

Preparation of (−)—(S)-1-(ethoxycarbonyl)ethyl Pivalate
(−)-Ethyl lactate (20.0 g, 0.17mole, $[\alpha]^{20}_D$=−10.5° (neat)) was esterified with pivaloyl chloride as described before. (B.p.$_{3mbars}$=83°, yield=77%)
$[\alpha]^{20}_D$=−26.6° (2.0%, CHCl$_3$).
$^1$H-NMR: 1.24 (s, 9H); 1.27 (t, J=7, 3H); 1.48 (d, J=7, 3H); 4.19 (m, 2H); 5.03 (q, J=7, 1H).
$^{13}$C-NMR: 14.1 (q), 16.8 (q), 27.0 (3q), 38.5 (s), 61.2 (t), 68.4 (d), 171.0 (s), 177.9 (s).

Example 2

Preparation of a Perfuming Composition
A perfuming composition for a detergent was prepared by admixing the following ingredients:

| Ingredient | Parts by weight |
|---|---|
| Isobornyl acetate | 40 |
| Dimethyl benzyl carbinyl acetate | 10 |
| Aldehyde C 12 | 3 |
| Aldehyde MNA | 2 |
| Methyl anthranilate | 10 |
| Benzyl acetone | 15 |
| Cetalox ®[1] | 10 |
| Citronellol | 100 |
| (1'R,E)-2-ethyl-4-(2',2',3'-trimethyl-3'-cyclopenten-1'-yl)-2-buten-1-ol[2] | 10 |
| Dihydromyrcenol | 40 |
| Doremox ®[3] | 5 |
| Hedione ®[4] | 25 |
| Heliotropine | 5 |
| Iralia Total ®[5] | 20 |
| Iso E Super ®[6] | 150 |
| Lavandin | 5 |
| Lemonile ®[7] | 5 |
| Mayol ®[8] | 20 |
| Methyl naphthyl ketone | 2 |
| 10%* Mousse Cristal | 15 |
| Neobutenone ®[9] Alpha | 3 |
| Trans-1-(2,2,6-trimethyl-1-cyclohexyl)-3-hexanol[2] | 5 |
| Rose oxide | 3 |
| Phenylhexanol | 30 |
| Verdyl propionate | 60 |
| Romascone ®[10] | 2 |
| Verdox ®[11] | 200 |
| 10%** Violettyne[12] | 5 |
| | 800 |

*in dipropyleneglycol
**in isopropyle myristate
[1] dodecahydro-3a,6,6,9a-tetramethyl-naphtho[2,1-b]furan; origin: Firmenich SA, Switzerland
[2] origin: Firmenich SA, Switzerland
[3] tetrahydro-4-methyl-2-phenyl-2H-pyran; origin: Firmenich SA, Switzerland
[4] methyl dihydrojasmonate; origin: Firmenich SA, Switzerland
[5] methyl ionones; origin: Firmenich SA, Switzerland
[6] 1-(octahydro-2,3,8,8-tetramethyl-2-naphthalenyl)-1-ethanone; origin: IFF, USA
[7] 3,7-dimethyl-2/3,6-nonadienenitrile; origin: Givaudan SA, Switzerland
[8] cis-7-P-menthanol; origin: Firmenich SA, Switzerland
[9] 1-(5,5-dimethyl-1-cyclohexen-1-yl)-4-penten-1-one; origin: Firmenich SA, Switzerland
[10] methyl 2,2-dimethyl-6-methylene-1-cyclohexanecarboxylate; origin: Firmenich SA, Switzerland
[11] 2-tert-butyl-1-cyclohexyl acetate; origin: IFF, USA
[12] 1,3-undecadien-5-yne; origin: Firmenich SA, Switzerland The addition of 50 parts by weight of (−)-propyl (2S)-2-(isobutyryloxy)propanoate imparted to the original perfuming base, which was devoid of any fruity note, a fruity velvety top note evoking a fresh apricot.

Example 3

Preparation of a Perfuming Composition
A perfuming composition for a eau de cologne for man was prepared by admixing the following ingredients:

| Ingredient | Parts by weight |
|---|---|
| 10%*Aldehyde MNA | 10 |
| Allyl Amyl Glycolate | 15 |
| Cedroxyde ®[1] | 120 |
| Coumarine | 5 |
| Damascone Alpha | 2 |
| Dihydroestragole | 3 |
| 10%* 7-Methyl-2H,4H-1,5-benzodioxepin-3-one[2] | 25 |
| Galbex ®[3] | 45 |
| Géranium essential oil | 20 |
| Habanolide ®[4] | 60 |
| Hedione ®[5] HC | 80 |
| Heliopropanal[2] | 10 |
| Iso E Super ®[6] | 140 |
| Lavandin | 50 |

-continued

| Ingredient | Parts by weight |
|---|---|
| Lyral ®[7] | 30 |
| Mousse Cristal | 10 |
| Muscenone ®[8] Delta | 10 |
| Nirvanol ®[9] | 30 |
| Trans-1-(2,2,6-trimethyl-1-cyclohexyl)-3-hexanol | 5 |
| 10%* Rose oxide | 10 |
| 1-Methyl-4-(4-methyl-3-pentenyl)-3-cyclohexene-1-carbaldehyde | 20 |
| Romandolide ®[10] | 110 |
| Amyl salicylate | 20 |
| Vertofix Coeur ®[11] | 50 |
| 10%* 2,4-Dimethyl-3-cyclohexene-1-carbaldehyde | 20 |
| | 900 |

*in dipropyleneglycol
[1] trimethyl-13-oxabicyclo-[10.1.0]-trideca-4,8-diene; origin: Firmenich SA, Switzerland
[2] origin: Firmenich SA, Switzerland
[3] perfuming composition; origin: Firmenich SA, Switzerland
[4] pentadecenolide; origin: Firmenich SA, Switzerland
[5] methyl dihydrojasmonate; origin: Firmenich SA, Switzerland
[6] 1-(octahydro-2,3,8,8-tetramethyl-2-naphthalenyl)-1-ethanone; origin: IFF, USA
[7] 4/3-(4-hydroxy-4-methylpentyl)-3-cyclohexene-1-carbaldehyde; origin: IFF, USA
[8] 3-methyl-(4/5)-cyclopentadecenone; origin: Firmenich SA, Switzerland
[9] 3,3-dimethyl-5-(2,2,3-trimethyl-3-cyclopenten-1-yl)-4-penten-2-ol; origin: Firmenich SA, Switzerland
[10] (1S,1'R)-[1-(3',3'-dimethyl-1'-cyclohexyl)ethoxycarbonyl]methyl propanoate; origin: Firmenich SA, Switzerland
[11] Methyl cedryl ketone; origin: IFF, USA The addition of 150 parts by weight of (−)-propyl (2S)-2-(isobutyryloxy)propanoate imparted to the original cologne a fruity freshness which married very well with the lavandin and which was very different from the note provided by the use of ethyl 2-acetoxoypropanoate, which imparted a green-herbaceous connotation.

What is claimed is:

1. A perfuming composition having fruity and/or floral odor notes devoid of a herbaceous note comprising:
   i) at least one compound of formula (I),

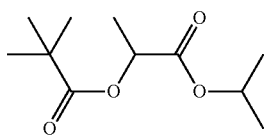

(I)

in the form of any one of its stereoisomers or a mixture thereof and present in an amount to confer or impart fruity and/or floral odor properties, devoid of a herbaceous note, to the composition;
   ii) at least one ingredient selected from the group consisting of a perfumery carrier and a perfumery base; and
   iii) optionally at least one perfumery adjuvant.

2. The composition of claim 1, wherein the compound of formula (I) is (−)—(S)-1-isopropoxy-1-oxopropan-2-yl pivalate.

3. A perfuming consumer product that contains at least one compound of formula (I),

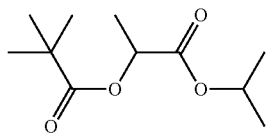

(I)

in the form of any one of its stereoisomers or a mixture thereof and in an amount sufficient to confer or impart fruity and/or floral odor properties, devoid of a herbaceous note, to the perfuming consumer product.

4. The perfuming consumer product of claim 3, which also contains at least one ingredient selected from the group consisting of a perfumery carrier and a perfumery base.

5. The perfuming consumer product of claim 4, which also contains at least one perfumery adjuvant.

6. The perfuming consumer product of claim 3, which is a perfume, a fabric care product, a body-care product, an air care product or a home care product.

7. The perfuming consumer product of claim 3, which is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil, or gel, a hygiene product, an air freshener, a powdered air freshener, a wipe, a dish detergent or hard-surface detergent.

8. In a perfuming composition or perfuming consumer product, the improvement which comprises providing therein the compound (−)—(S)-1-isopropoxy-1-oxopropan-2-yl pivalate in an amount sufficient to confer or impart fruity and/or floral odor properties to the perfuming composition or perfuming consumer product.

9. The perfuming composition or perfuming consumer product of claim 8, wherein the perfuming composition is provided as a combination of the compound, at least one ingredient selected from the group consisting of a perfumery carrier and a perfumery base, and at least one perfumery adjuvant.

10. The perfuming composition or perfuming consumer product of claim 8, wherein the compound is provided in a perfuming consumer product that is a perfume, a fabric care product, a body-care product, an air care product or a home care product.

11. The perfuming composition or perfuming consumer product of claim 8, wherein the compound is provided in a perfuming consumer product that is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil, or gel, a hygiene product, an air freshener, a powdered air freshener, a wipe, a dish detergent or hard-surface detergent.

* * * * *